United States Patent [19]
Vogler et al.

[11] Patent Number: 5,344,611
[45] Date of Patent: Sep. 6, 1994

[54] VACUUM ACTUATED BLOOD COLLECTION ASSEMBLY INCLUDING TUBE OF CLOT-ACCELERATING PLASTIC

[75] Inventors: Erwin A. Vogler, Newhill; Garry R. Harper, Raleigh; Jane C. Graper, Durham, all of N.C.

[73] Assignee: Becton, Dickinson and Company, Franklin Lakes, N.J.

[21] Appl. No.: 75,441

[22] Filed: Jun. 14, 1993

[51] Int. Cl.$^5$ .................. B01L 11/00; A61M 1/00
[52] U.S. Cl. ................... 422/101; 128/760; 128/763; 128/765; 128/770; 422/102; 604/317; 604/411; 604/414
[58] Field of Search .............. 422/101, 102, 61, 102; 430/247, 205, 317; 428/35, 36.9, 423.1, 447, 483; 128/760, 763, 765, 770; 604/317, 411, 414

[56] References Cited

U.S. PATENT DOCUMENTS

| | | | |
|---|---|---|---|
| 4,207,286 | 6/1980 | Gut Boucher | 422/21 |
| 4,294,707 | 10/1981 | Ikeda et al. | 422/101 |
| 4,482,585 | 11/1984 | Ohodaira et al. | 428/35 |
| 4,967,763 | 11/1990 | Nugents et al. | 128/763 |
| 4,980,129 | 12/1990 | Columbus | 422/61 |
| 4,980,231 | 12/1990 | Baker et al. | 428/36.9 |
| 5,043,244 | 8/1991 | Cairncross et al. | 430/247 |

*Primary Examiner*—Timothy M. McMahon
*Attorney, Agent, or Firm*—Richard E. Brown

[57] ABSTRACT

An evacuated blood collection assembly includes a plastic container having a plasma-treated inside wall surface and an open end covered by a puncturable septum. The inside wall surface may also be abraded to increase surface area. The invention included a method to make the assembly.

10 Claims, 3 Drawing Sheets

VACUUM ACTUATED BLOOD COLLECTION ASSEMBLY INCLUDING TUBE OF CLOT-ACCELERATING PLASTIC

BACKGROUND OF THE INVENTION

1. Field of the Invention

This invention relates to blood collection and, more particularly, relates to a plastic blood sample collection assembly.

2. Background

Blood samples are routinely taken in evacuated tubes, such as glass VACUTAINER TM tubes (Becton, Dickinson and Company). One end of a double-ended needle is inserted into a patient's vein. The other end of the needle then punctures a septum covering the open end of the VACUTAINER TM tube so that the vacuum in the tube draws the blood sample through the needle into the tube. Using this technique, a plurality of samples can be taken using a single needle puncture of the skin. Plastic tubes have also been proposed for blood collection. Plastic offers a number of advantages over glass such as lower breakage, less weight in shipment, and easier disposal by incineration.

Blood collected in evacuated tubes often must be clotted prior to clinical examination. It is desirable to form a dense clot as rapidly and completely as possible to facilitate clean separation of the clot from the serum layer by centrifugation. To achieve this end, both plastic and glass blood collection tubes frequently employ a clot activator. Typical activators are diatomaceous earth and particles of inorganic silicates, or biochemicals such as ellagic acid and thromboplastin. In one line of commercial blood collection tubes, for example, a coating of silicate particles in polyvinylpyrrolidone (PVP, a water soluble polymer) is affixed to the inside of the tube. When blood enters the tube, the PVP dissolves and silicate particles are released to initiate clotting. The PVP enters both the serum and clot.

A problem with particulate activators is that finely divided particles may not pellet completely with the clot and may thus contaminate the serum layer and interfere with certain blood analyses. In addition, particles suspended in the serum may foul automatic blood analysis instruments. On the other hand, soluble biochemical activators can be disadvantageous because these cannot be easily separated from either the serum or blood clot and can interfere with both chemical and hematological assays. In particular, for highly specialized applications, such as blood banking, it is unacceptable to have either soluble activators or particulates in the cell mass of a blood clot because these cells are used in blood typing analyses. For this reason, samples for blood banking are routinely taken in glass tubes and rely on the clot activating property of the glass to induce clotting. There is a need in the art of blood collection for equipment which provides an enhanced rate of blood coagulation without leaving any soluble or particulate material in the serum layer or in the clot on centrifugation, thus avoiding potential interference with clinical tests, and particularly in blood banking procedures. The present invention is directed to fulfilling this need.

SUMMARY OF THE INVENTION

A blood collection assembly includes a tube having a bottom wall continuous with a side wall. The side wall defines an open end and the bottom wall defines a closed end. Together the bottom and side walls define an inside wall surface. The open end is covered by a puncturable septum, and the tube is evacuated. The inside wall surface is treated with a plasma from a process gas and may additionally be abraded to have greater surface area.

A second aspect of the invention is a method to make the assembly of the invention. In one embodiment of the method, the inside wall of the tube is treated with a plasma to introduce a heteroatom to the surface of the wall. In a second method embodiment, the inside wall surface is abraded to be rough for greater surface area. In the preferred method, the inside wall of the tube is both abraded and plasma-treated.

Thus the invention provides a plastic tube which retains the advantages of plastic and overcomes the disadvantage of poor and slow coagulation in plastic. The plasma treatment and abrasion modify the chemistry of the inside wall of the tube so that clotting is accelerated but no particulate or soluble clotting activators or binders are present to contaminate either the serum or the clot. The assembly of the invention is particularly well suited for blood bank operations.

DETAILED DESCRIPTION

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

Figure 1:
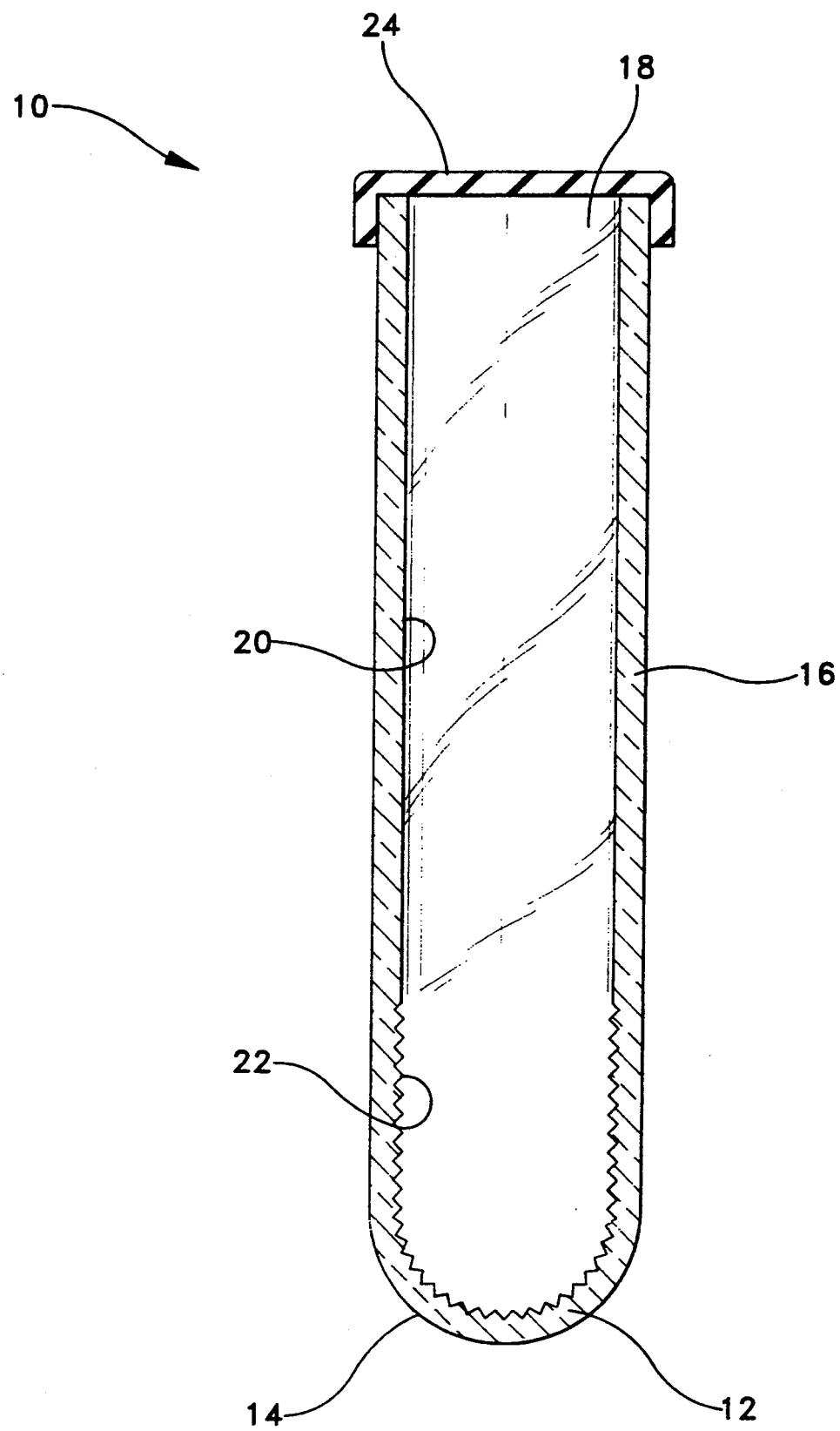
FIG. 1 is a perspective view of the blood collection assembly of the invention.

The blood collection assembly of the invention may include any container having a closed end and an open end. Suitable containers are, for example bottles, vials, flasks and the like, preferably tubes. The invention will henceforth be described in terms of the preferred tube. FIG. 1 illustrates the tube of the invention. A tube 10 has a bottom wall 12 defining a closed end 14 and a side wall 16 defining an open end 18. Bottom wall 12 and side wall 14 are continuous and together define an inside wall surface 20. An area 22 of inside wall surface 20 is rough as a result of being abraded. While FIG. 1 shows only a portion of the inside wall near the bottom of the tube to be rough, this is merely the preferred embodiment of the invention which maintains the upper portion of the tube fully transparent for clear visibility of the serum layer. It is of course evident that, if desired, the entire inside surface or any other portion thereof could be abraded. The open end 18 of tube 10 is covered with puncturable septum 24. Tube 10 covered by septum 24 is evacuated. Evacuated tubes for blood collection are standard in the art as, for example, VACUTAINER TM brand tubes (Becton, Dickinson and Company).

The tube may be of plastic. Suitable plastics are polyethylene terephthalate (PET) and preferably polystyrene (PS). While the tube may be of any size, the invention is particularly well suited to evacuated blood collection tubes.

These tubes are generally cylindrical, 50 to 150 mm in length and about 10 to 20 mm in diameter.

In accordance with the invention, it has been found that treatment of the tube with a plasma results in a surprising increase in the rate of clotting of a blood sample. The plasma may be generated from any suitable process gas. A representative but not limiting list of suitable process gases includes nitrogen, ammonia, carbon dioxide, sulfur dioxide, air and oxygen wherein air and oxygen are preferred. The tube may be placed open end up between the electrodes of a conventional plasma generator equipped with a pressure gauge, a gas inbleed and a vacuum connection. Suitable electrodes may be of any conducting material, although stainless steel and aluminum are preferred. The width and shape of the electrodes is not critical. Any suitable ionizing plasma may be used, as, for example, a plasma generated by a corona discharge or preferably a glow discharge.

A wide range of power settings, radio frequencies and duration of exposure of the plastic surface to the plasma may be used. Ranges for these parameters which provide advantageous results are DC or AC power levels up to 200 watts, from about 0.1 to about 50 megahertz and from about 0.1 to 30 minutes. Preferred ranges are 10–50 watts, 10–20 megahertz and 2–10 minutes respectively. Any gas pressure may be used, however, gas pressures are advantageously maintained at 5 mm of Hg or below in order to benefit from reduced voltage requirements. Ambient temperature for plasma generation is preferred.

The plasma treatment results in introduction of polar functional groups into the surface of the plastic. The functional group depends on the process gas used to generate the plasma. For example, after plasma treatment, the surface may contain oxygen, nitrogen or sulfur atoms. These groups cause the plasma-treated surface to have a clot activating property similar to and even somewhat greater than that of glass. The examples and the drawings show the accelerated clotting rates of the plasma-treated plastic surfaces relative to those of glass and untreated plastic.

In the preferred embodiment of the invention, the inside wall surface of the tube is abraded to have a rough surface and thereby an increased surface area. The plasma treatment may be performed prior to or preferably subsequent to abrading. The surface may be roughened by any conventional chemical or mechanical method, or during the tube forming process. Most conveniently, the surface is merely rubbed with an abrasive, such as with sand or emery paper. No limitation is placed on the grit of the abrasive, although it has been found that a medium grit sandpaper gives the greatest increase in surface area. Most preferably, the portion of the inside wall surface at or near the bottom of the tube is roughened, and the remainder of the tube is not roughened, as this maintains the maximum clarity of the tube for observation of the serum layer after centrifugation. It is, of course, understood that the entire inside wall surface is preferably treated with the plasma.

EXAMPLE I

Clot activating properties of the plasma treated tubes of the invention were assessed by comparison of the time required to clot platelet poor plasma (PPP) or whole porcine (pig) blood to that in untreated PS and glass tubes. PPP was prepared by separating cells by centrifugation of citrated porcine blood (Environmental Diagnostics Inc.). Approximately 3 ml of PPP or whole blood were added to the tubes and temperature was equilibrated to room temperature in a water bath for 15 minutes. Following equilibration, 200 $\mu l$ of 0.2 M $CaCl_2$ per ml or PPP or blood was added to initiate coagulation. Tube contents were mixed on a laboratory inverting mixer and time of clotting noted for each tube type. Clotted PPP or whole blood was distinguished from nonclotted by an obvious change from a fluid state to a gelatinous state which did not flow in the tube on rotation. Clotting time was measured at this point.

EXAMPLE II

Plasma Treatment

A. A PS tube (Becton Dickinson, FALCON TM, 13 mm×75 mm) was exposed to an oxygen plasma generated in a conventional planar diode plasma unit operated at about 50 watts of an RF frequency of 13.56 megahertz at a pressure of 200–300 mTorr for about 5 minutes to produce a highly oxidized surface chemistry.

Figure 2:
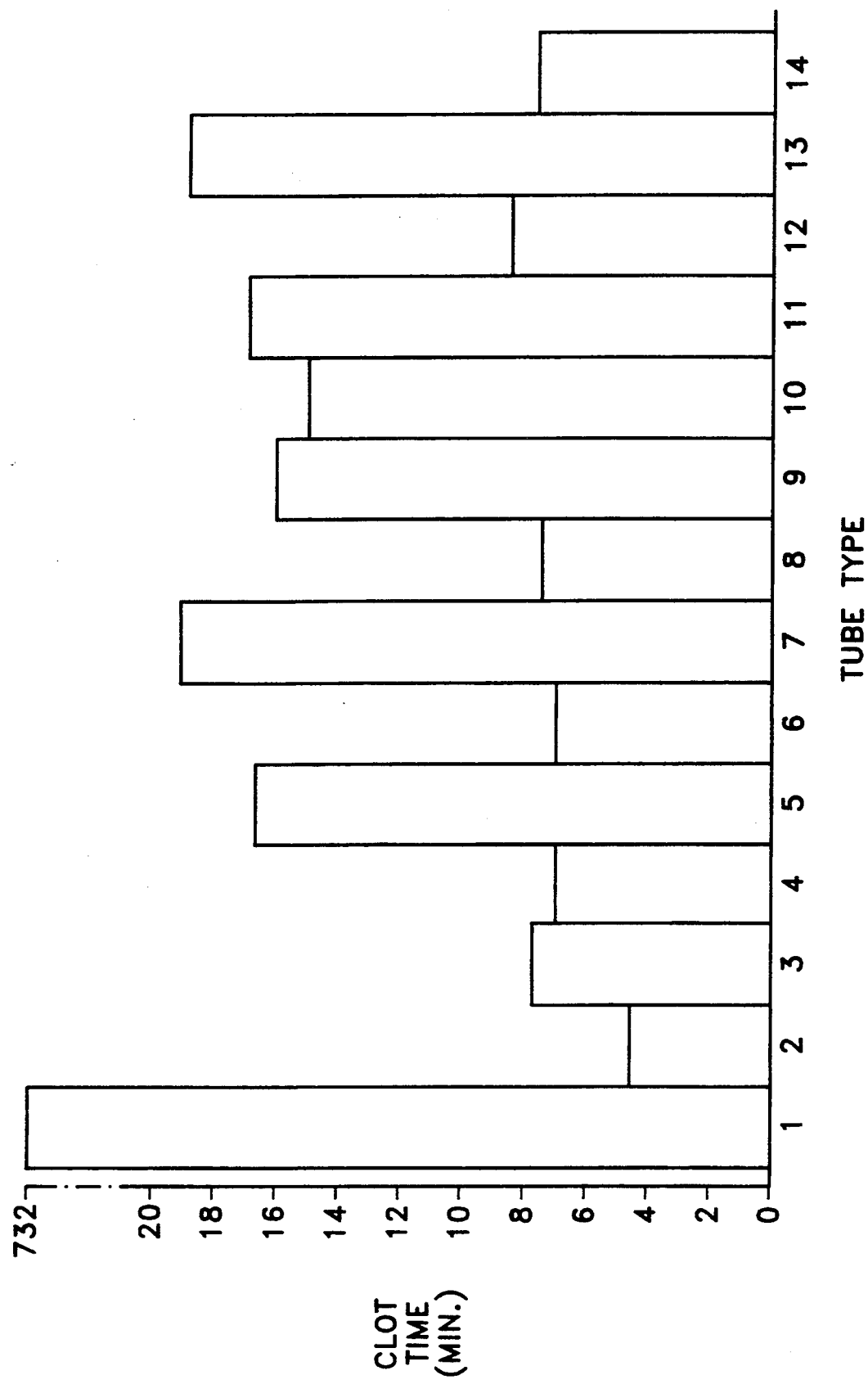
FIGS. 2 and 3 compare the rate of blood clotting in representative tubes of the invention with control tubes.

B. In the same way as in A, a tube of impact modified PS (K resin, Phillips), a polypropylene (PP) tube (ESCORENE TM, Exxon) and PET tubes (Eastman grades 2182 and 1042) were plasma treated. Clot activation properties of the tubes of the invention and control tubes are set forth in FIG. 2 in which the tube types are as follows:

Using whole blood:
1. PS FALCON TM
2. PS FALCON TM plasma treated

Using PPP:
3. glass
4. glass plasma treated
5. PS FALCON TM
6. PS FALCON TM plasma treated
7. PS K resin
8. PS K resin plasma treated
9. PP
10. PP plasma treated
11. PET 2182
12. PET 2182 plasma treated
13. PET 1042
14. PET 1042 plasma treated It is seen from FIG. 2 that plasma treatment of PS tubes lowers the clot time of whole blood by more than 8 fold (tube types 1 and 2). Clot time of PPP in plasma treated PS is reduced by about 2.5 fold compared to non-plasma treated PS (tubes 5–8). Clot time of PPP is also reduced about 2–2.5 fold in PET tubes (tubes 11–14) on plasma treatment, but plasma treatment of PP had substantially no effect on PPP clotting (tubes 9 and 10).

EXAMPLE III

Figure 3:
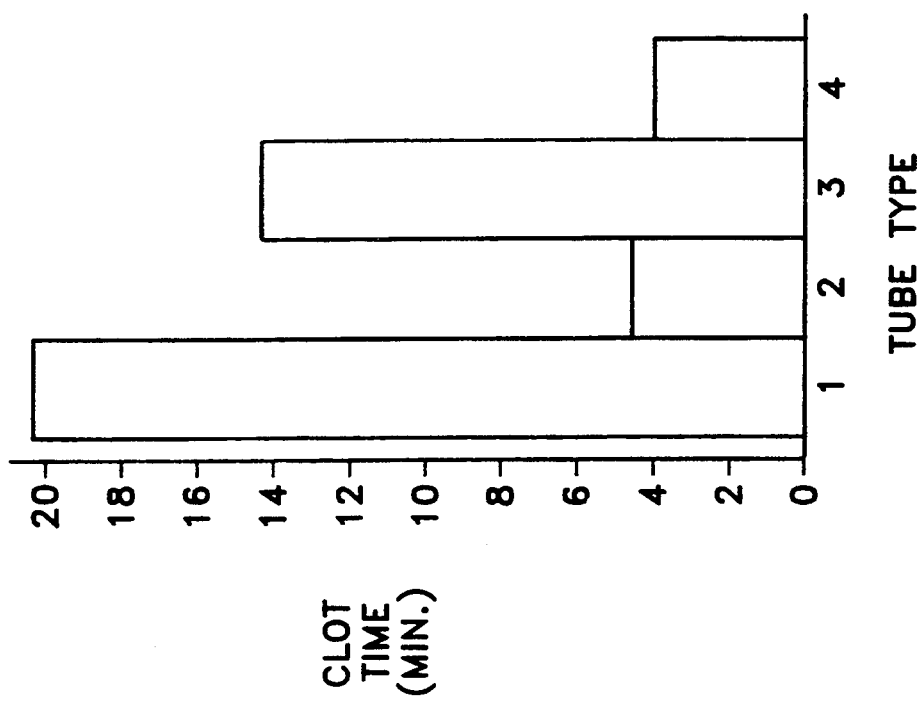

The lower half of PS tubes (FALCON TM) were mechanically abraded using medium-grit sandpaper to give a rough interior wall surface. FIG. 3 compares clot time observed in these tubes before and after plasma oxidation performed as described in Example II. In FIG. 3, the tube types are as follows:
1. PS FALCON TM
2. PS FALCON TM plasma treated
3. PS FALCON TM abraded
4. PS FALCON TM abraded and plasma treated It is seen that abrading to give a rough surface of higher surface area reduces clot time to PPP by about 30% (tube 3 compared to control tube 1 ), and that plasma treatment of the roughened surface (tube 4) reduces clot time by a factor of 5 compared to control tube 1.

What is claimed is:

1. A blood collection assembly comprising a plastic blood collection container having a bottom wall and a side wall defining an open end covered by a puncturable septum, said bottom wall, side wall and septum enclosing an evacuated interior volume of said container, an interior wall surface area of said container being treated with a plasma from a process gas, the plasma-treated wall surface having an accelerated rate of blood clotting in said container relative to the rate in an otherwise identical non-plasma-treated container.

2. The assembly of claim 1 wherein said container is fabricated of a plastic selected from the group consisting of polystyrene, impact modified polystyrene and polyethylene terephthalate.

3. The assembly of claim 1 wherein said process gas is selected from the group consisting of air, oxygen, nitrogen, ammonia, carbon dioxide and sulfur dioxide.

4. A blood collection assembly comprising a plastic blood collection container having a bottom wall and a side wall defining an open end covered by a puncturable septum, said bottom wall, side wall and septum enclosing an evacuated interior volume of said container, an interior wall surface area of said container being abraded to have a rough surface and treated with a plasma from a process gas, the abraded and plasma-treated wall surface causing an accelerated rate of blood clotting in said container relative to the rate in an otherwise identical non-abraded, non-plasma-treated container.

5. The assembly of claim 4 wherein said container is polystyrene and said process gas is oxygen.

6. A method for preparing a plastic blood collection assembly comprising:
   a) exposing an inside wall surface of a plastic container having an open end to a plasma from a process gas to give a plasma-treated inside wall surface;
   b) covering said open end with a puncturable septum; and
   c) evacuating the container covered by said septum, said plasma-treated wall surface having an accelerated rate of blood clotting relative to the rate in an otherwise identical non-plasma-treated container.

7. The method of claim 6 wherein said container is fabricated of a plastic selected from the group consisting of polystyrene, impact modified polystyrene and polyethylene terephthalate.

8. The method of claim 6 wherein said process gas is selected from the group consisting of air, oxygen, nitrogen, ammonia, carbon dioxide and sulfur dioxide.

9. A method for preparing a plastic blood collection assembly comprising:
   a) abrading an inside wall surface of a plastic container having an open end to give a roughened inside wall surface having a greater surface area than that of said plastic container prior to said abrading;
   b) exposing said roughened inside wall surface to a plasma from a process gas;
   c) covering said open end with a puncturable septum; and
   d) evacuating the container covered by said septum.

10. The method of claim 9 wherein said container is polystyrene and said process gas is oxygen.

* * * * *